US010765592B2

(12) United States Patent
Locke et al.

(10) Patent No.: US 10,765,592 B2
(45) Date of Patent: *Sep. 8, 2020

(54) SYSTEM AND METHOD FOR DETERMINING A FILL STATUS OF A CANISTER OF FLUID IN A REDUCED PRESSURE TREATMENT SYSTEM

(71) Applicant: KCI Licensing, Inc., San Antonio, TX (US)

(72) Inventors: Christopher Brian Locke, Bournemouth (GB); Timothy Mark Robinson, Shillingstone (GB); David Robson Blandford, Alderholt (GB)

(73) Assignee: KCI Licensing, Inc., San Antonio, TX (US)

( * ) Notice: Subject to any disclaimer, the term of this patent is extended or adjusted under 35 U.S.C. 154(b) by 319 days.

This patent is subject to a terminal disclaimer.

(21) Appl. No.: 15/812,337

(22) Filed: Nov. 14, 2017

(65) Prior Publication Data

US 2018/0064601 A1 Mar. 8, 2018

Related U.S. Application Data

(60) Continuation of application No. 14/925,461, filed on Oct. 28, 2015, now Pat. No. 9,844,485, which is a
(Continued)

(51) Int. Cl.
*A61H 9/00* (2006.01)
*A61M 1/00* (2006.01)
(Continued)

(52) U.S. Cl.
CPC ......... *A61H 9/0057* (2013.01); *A61M 1/0001* (2013.01); *A61M 1/0023* (2013.01);
(Continued)

(58) Field of Classification Search
CPC ......... A61H 2201/5056; A61H 9/0057; A61M 1/0001; A61M 1/0023; A61M 1/0025;
(Continued)

(56) References Cited

U.S. PATENT DOCUMENTS 1,355,846 A 10/1920 Rannells
1,885,926 A * 11/1932 Lewis .................. G01F 23/16
73/290 B
(Continued)

FOREIGN PATENT DOCUMENTS

AU 550575 B2 3/1986
AU 745271 B2 3/2002
(Continued)

OTHER PUBLICATIONS

EP17159742.0 corresponding to EP Extended Search Report, dated Aug. 1, 2017.
(Continued)

*Primary Examiner* — Adam Marcetich

(57) ABSTRACT

A reduced pressure treatment system is provided that includes a canister that is fluidly connected to a tissue site and is configured to receive fluid drawn from the tissue site under the influence of a reduced pressure. A reduced pressure source provides the reduced pressure and is fluidly connected to the tissue site by a fluid communication path, which may include a source conduit, the canister, and a target conduit. A sensing device communicates with the source conduit and is configured to sense a pressure in the source conduit. A valve communicates with the source conduit and is configured to vent the reduced pressure. A processing unit communicates with the sensing device and the valve and is configured to open the valve for a selected
(Continued)

amount of time, determine a decay of reduced pressure, and determine a fill status of the canister based on the decay of reduced pressure.

18 Claims, 4 Drawing Sheets

Related U.S. Application Data continuation of application No. 14/265,571, filed on Apr. 30, 2014, now Pat. No. 9,199,011, which is a continuation of application No. 13/733,778, filed on Jan. 3, 2013, now Pat. No. 8,747,376, which is a division of application No. 11/901,664, filed on Sep. 18, 2007, now Pat. No. 8,366,690.

(60) Provisional application No. 60/845,993, filed on Sep. 19, 2006.

(51) Int. Cl.
| | | |
|---|---|---|
| *G01F 23/14* | (2006.01) | |
| *A61M 5/14* | (2006.01) | |
| *A61N 1/04* | (2006.01) | |
| *A61N 5/06* | (2006.01) | |
| *F16M 11/04* | (2006.01) | |
| *F16M 13/02* | (2006.01) | |

(52) U.S. Cl.
CPC ........ *A61M 1/0025* (2014.02); *A61M 1/0031* (2013.01); *A61M 1/0088* (2013.01); *A61M 5/1415* (2013.01); *A61N 1/0468* (2013.01); *A61N 5/0616* (2013.01); *F16M 11/046* (2013.01); *F16M 11/048* (2013.01); *F16M 13/02* (2013.01); *G01F 23/14* (2013.01); *A61H 2201/5056* (2013.01); *A61M 2205/15* (2013.01); *A61M 2205/33* (2013.01); *A61M 2205/3327* (2013.01); *A61M 2205/3331* (2013.01); *A61M 2205/3337* (2013.01); *A61M 2205/3379* (2013.01); *A61M 2205/3382* (2013.01); *A61M 2205/3389* (2013.01); *A61M 2205/43* (2013.01); *A61M 2205/581* (2013.01); *A61N 2005/0661* (2013.01); *F16M 2200/027* (2013.01)

(58) Field of Classification Search
CPC .............. A61M 1/0031; A61M 1/0088; A61M 2205/15; A61M 2205/33; A61M 2205/3327; A61M 2205/3331; A61M 2205/3337; A61M 2205/3379; A61M 2205/3382; A61M 2205/3389; A61M 2205/43; A61M 2205/581; A61M 5/1415; A61N 1/0468; A61N 2005/0661; A61N 5/0616; F16M 11/046; F16M 11/048; F16M 13/02; F16M 2200/027; G01F 23/14

See application file for complete search history.

(56) References Cited

U.S. PATENT DOCUMENTS

| | | | |
|---|---|---|---|
| 2,547,758 A | | 4/1951 | Keeling |
| 2,632,443 A | | 3/1953 | Lesher |
| 2,682,873 A | | 7/1954 | Evans et al. |
| 2,696,113 A | * | 12/1954 | Prescott ................ G01F 15/08 73/861.04 |
| 2,910,763 A | | 11/1959 | Lauterbach |
| 2,969,057 A | | 1/1961 | Simmons |
| 3,012,772 A | | 12/1961 | Gunzner |
| 3,066,672 A | | 12/1962 | Crosby, Jr. et al. |
| 3,367,332 A | | 2/1968 | Groves |
| 3,520,300 A | | 7/1970 | Flower, Jr. |
| 3,568,675 A | | 3/1971 | Harvey |
| 3,648,692 A | | 3/1972 | Wheeler |
| 3,682,180 A | | 8/1972 | McFarlane |
| 3,826,254 A | | 7/1974 | Mellor |
| 3,902,495 A | | 9/1975 | Weiss et al. |
| 4,018,908 A | | 4/1977 | Gross |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | | 3/1981 | Nichols |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,333,468 A | | 6/1982 | Geist |
| 4,338,945 A | | 7/1982 | Kosugi et al. |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,465,485 A | | 8/1984 | Kashmer et al. |
| 4,475,909 A | | 10/1984 | Eisenberg |
| 4,480,638 A | | 11/1984 | Schmid |
| 4,509,959 A | | 4/1985 | McCombs |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,547,092 A | | 10/1985 | Vetter et al. |
| 4,548,202 A | | 10/1985 | Duncan |
| 4,551,139 A | | 11/1985 | Plaas et al. |
| 4,553,431 A | | 11/1985 | Nicolai |
| 4,569,348 A | | 2/1986 | Hasslinger |
| 4,569,674 A | | 2/1986 | Phillips et al. |
| 4,583,546 A | | 4/1986 | Garde |
| 4,605,399 A | | 8/1986 | Weston et al. |
| 4,608,041 A | | 8/1986 | Nielsen |
| 4,608,857 A | * | 9/1986 | Mertens ............... G01M 3/2815 73/40.5 R |
| 4,640,688 A | | 2/1987 | Hauser |
| 4,651,743 A | | 3/1987 | Stoller |
| 4,655,754 A | | 4/1987 | Richmond et al. |
| 4,664,662 A | | 5/1987 | Webster |
| 4,673,272 A | | 6/1987 | Suzuki et al. |
| 4,710,165 A | | 12/1987 | McNeil et al. |
| 4,733,659 A | | 3/1988 | Edenbaum et al. |
| 4,743,232 A | | 5/1988 | Kruger |
| 4,758,220 A | | 7/1988 | Sundblom et al. |
| 4,785,659 A | | 11/1988 | Rose et al. |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kalt |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,073,172 A | * | 12/1991 | Fell ..................... A61M 1/0003 604/119 |
| 5,086,170 A | | 2/1992 | Luheshi et al. |
| 5,092,858 A | | 3/1992 | Benson et al. |
| 5,100,396 A | | 3/1992 | Zamierowski |
| 5,108,213 A | | 4/1992 | Shields |

(56) References Cited

U.S. PATENT DOCUMENTS

| | | |
|---|---|---|
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,195,995 A | 3/1993 | Walker |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,310,524 A | 5/1994 | Campbell et al. |
| 5,342,376 A | 8/1994 | Ruff |
| 5,343,878 A | 9/1994 | Scarberry et al. |
| 5,344,415 A | 9/1994 | DeBusk et al. |
| 5,358,494 A | 10/1994 | Svedman |
| 5,407,310 A | 4/1995 | Kassouni |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,658,322 A | 8/1997 | Fleming |
| 5,690,815 A | 11/1997 | Krasnoff et al. |
| 5,718,562 A | 2/1998 | Lawless et al. |
| 5,749,842 A | 5/1998 | Cheong et al. |
| 5,752,688 A | 5/1998 | Campbell et al. |
| 5,852,675 A | 12/1998 | Matsuo et al. |
| 5,862,803 A | 1/1999 | Besson et al. |
| 5,911,687 A | 6/1999 | Sato et al. |
| 5,986,163 A | 11/1999 | Augustine |
| 6,032,678 A | 3/2000 | Rottem |
| 6,036,296 A * | 3/2000 | Axtell .................. B41J 2/17513 347/7 |
| 6,047,259 A | 4/2000 | Campbell et al. |
| 6,057,689 A | 5/2000 | Saadat |
| 6,071,267 A | 6/2000 | Zamierowski |
| 6,091,981 A | 7/2000 | Cundari et al. |
| 6,134,003 A | 10/2000 | Tearney et al. |
| 6,135,116 A | 10/2000 | Vogel et al. |
| 6,142,982 A | 11/2000 | Hunt et al. |
| 6,208,749 B1 | 3/2001 | Gutkowicz-Krusin et al. |
| 6,241,747 B1 | 6/2001 | Ruff |
| 6,287,316 B1 | 9/2001 | Agarwal et al. |
| 6,292,866 B1 | 9/2001 | Zaiki et al. |
| 6,345,623 B1 | 2/2002 | Heaton et al. |
| 6,378,826 B1 | 4/2002 | Knaub et al. |
| 6,447,537 B1 | 9/2002 | Hartman |
| 6,453,247 B1 | 9/2002 | Hunaidi |
| 6,458,109 B1 | 10/2002 | Henley et al. |
| 6,471,197 B1 | 10/2002 | Denk et al. |
| 6,488,643 B1 | 12/2002 | Tumey et al. |
| 6,493,568 B1 | 12/2002 | Bell et al. |
| 6,529,006 B1 | 3/2003 | Hayes |
| 6,553,998 B2 | 4/2003 | Heaton et al. |
| 6,648,862 B2 | 11/2003 | Watson |
| 6,663,586 B2 | 12/2003 | Verkaart et al. |
| 6,733,537 B1 | 5/2004 | Fields et al. |
| 6,814,079 B2 | 11/2004 | Heaton et al. |
| 6,915,950 B1 | 7/2005 | Legerstee |
| 7,004,915 B2 | 2/2006 | Boynton et al. |
| 7,100,244 B2 | 9/2006 | Qin et al. |
| 7,198,046 B1 | 4/2007 | Argenta et al. |
| 7,770,855 B2 | 8/2010 | Locke et al. |
| 7,846,141 B2 | 12/2010 | Weston |
| 7,857,271 B2 | 12/2010 | Lees |
| 7,876,546 B2 | 1/2011 | Locke et al. |
| 8,000,777 B2 | 8/2011 | Jaeb et al. |
| 8,057,449 B2 | 11/2011 | Sanders et al. |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,366,690 B2 | 2/2013 | Locke et al. |
| 8,398,614 B2 | 3/2013 | Blott et al. |
| 8,449,509 B2 | 5/2013 | Weston |
| 8,500,718 B2 | 8/2013 | Locke et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,690,845 B2 | 4/2014 | Long et al. |
| 8,696,662 B2 | 4/2014 | Eder et al. |
| 8,786,999 B2 | 7/2014 | Locke et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,019,681 B2 | 4/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,320,673 B2 | 4/2016 | Locke et al. |
| 2002/0019751 A1 | 2/2002 | Rothschild et al. |
| 2002/0077661 A1 | 6/2002 | Saadat |
| 2002/0095198 A1 | 7/2002 | Whitebook et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0198503 A1 | 12/2002 | Risk et al. |
| 2002/0198504 A1 | 12/2002 | Risk et al. |
| 2003/0022645 A1 | 1/2003 | Runzo |
| 2003/0085908 A1 | 5/2003 | Luby |
| 2003/0182806 A1 | 10/2003 | Luebke et al. |
| 2003/0226943 A1 | 12/2003 | Laisement et al. |
| 2004/0008523 A1 | 1/2004 | Butler |
| 2004/0070535 A1 | 4/2004 | Olsson et al. |
| 2004/0073151 A1 | 4/2004 | Weston |
| 2004/0078236 A1 | 4/2004 | Stoodley et al. |
| 2004/0122705 A1 | 6/2004 | Sabol et al. |
| 2004/0138632 A1 | 7/2004 | Bemis et al. |
| 2004/0143677 A1 | 7/2004 | Novak |
| 2004/0231414 A1* | 11/2004 | Delnevo .............. A61M 1/3624 73/290 R |
| 2005/0051168 A1 | 3/2005 | DeVries et al. |
| 2005/0090787 A1 | 4/2005 | Risk et al. |
| 2005/0102009 A1 | 5/2005 | Costantino |
| 2005/0115314 A1* | 6/2005 | Meagher ................ G01F 23/14 73/290 B |
| 2005/0120792 A1* | 6/2005 | Merrild ................. G01F 23/14 73/303 |
| 2005/0148913 A1 | 7/2005 | Weston |
| 2005/0203469 A1 | 9/2005 | Bobroff et al. |
| 2005/0261642 A1 | 11/2005 | Weston |
| 2006/0027979 A1 | 2/2006 | Yang et al. |
| 2006/0072804 A1 | 4/2006 | Watson et al. |
| 2006/0074722 A1 | 4/2006 | Chu |
| 2006/0131350 A1* | 6/2006 | Schechter ........... A61M 15/009 222/645 |
| 2006/0189887 A1 | 8/2006 | Hassler et al. |
| 2006/0195625 A1 | 8/2006 | Hesse |
| 2007/0000310 A1 | 1/2007 | Yamartino et al. |
| 2007/0032763 A1 | 2/2007 | Vogel |
| 2007/0053554 A1 | 3/2007 | Fayad et al. |
| 2007/0125170 A1* | 6/2007 | Tenney ................. G01F 23/14 73/290 R |
| 2007/0265586 A1 | 11/2007 | Joshi et al. |
| 2008/0008370 A1 | 1/2008 | Chio |
| 2008/0260218 A1 | 10/2008 | Smith et al. |
| 2008/0275409 A1 | 11/2008 | Kane et al. |
| 2008/0281281 A1 | 11/2008 | Meyer et al. |
| 2009/0120165 A1 | 5/2009 | Lang et al. |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |

(56) References Cited

FOREIGN PATENT DOCUMENTS

| | | |
|---|---|---|
| DE | 43 06 478 A1 | 9/1994 |
| DE | 29 504 378 U1 | 9/1995 |
| DE | 29920378 U1 | 3/2000 |
| EP | 0100148 A1 | 2/1984 |
| EP | 0117632 A2 | 9/1984 |
| EP | 0161865 A2 | 11/1985 |
| EP | 0224367 A2 | 6/1987 |
| EP | 0358302 A2 | 3/1990 |
| EP | 0836831 A2 | 4/1998 |
| EP | 1018967 A1 | 7/2000 |
| EP | 1591713 A1 | 11/2005 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2356148 A | 5/2001 |
| JP | 1129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 94/21312 A2 | 9/1994 |
| WO | 96/05873 A1 | 2/1996 |
| WO | 97/18007 A1 | 5/1997 |
| WO | 97047235 A1 | 12/1997 |
| WO | 1998025122 A1 | 6/1998 |
| WO | 99/13793 A1 | 3/1999 |
| WO | 9949775 A2 | 10/1999 |
| WO | 2000021586 A1 | 4/2000 |
| WO | 02080764 A1 | 10/2002 |
| WO | 2005060466 A2 | 7/2005 |
| WO | 2005061025 A1 | 7/2005 |
| WO | 2006052745 A2 | 5/2006 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

(56) References Cited

OTHER PUBLICATIONS

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

Extended European Search Report for corresponding EP07838545.7, dated Aug. 2, 2013.

Brazilian Preliminary Examination Report for corresponding Application No. PI0714531-4, dated Feb. 26, 2019.

Indian Hearing Notice for corresponding Application No. 2076/CHENP/2009, dated Jul. 30, 2018.

Brazilian Technical Opinion for corresponding Application No. PI0714993-0, dated Jun. 14, 2018.

Indian First Examination Report corresponding to Application No. 2076/CHENP/2009, dated Jul. 14, 2017.

European Extended Search Report corresponding to EP 17157187.0 dated Jul. 21, 2017.

European Examination Report for corresponding Application No. 078385614, dated May 25, 2016.

Indian Exam Report for corresponding application 2074CHENP2009, dated Sep. 25, 2017.

Extended European Search Report for corresponding Application No. 171794498, dated Nov. 8, 2017.

Brazilian Preliminary Examination Report for Corresponding Application No. PI 0715020-2, dated Jun. 30, 2020.

\* cited by examiner

SYSTEM AND METHOD FOR DETERMINING A FILL STATUS OF A CANISTER OF FLUID IN A REDUCED PRESSURE TREATMENT SYSTEM

CROSS-REFERENCE TO RELATED APPLICATIONS

This application is a continuation of U.S. application Ser. No. 14/925,461, filed Oct. 28, 2015 which is a continuation of U.S. application Ser. No. 14/265,571, filed Apr. 30, 2014 now U.S. Pat. No. 9,199,011 which is a continuation of U.S. application Ser. No. 13/733,778, filed Jan. 3, 2013 now U.S. Pat. No. 8,747,376 which is a divisional of U.S. Non Provisional application Ser. No. 11/901,664 filed Sep. 18, 2007 now U.S. Pat. No. 8,366,690 which claims the benefit of U.S. Provisional Application No. 60/845,993, filed Sep. 19, 2006, which is hereby incorporated by reference.

BACKGROUND OF THE INVENTION

1. Field of the Invention

The present invention relates generally to medical devices and more specifically to detection methods and systems for determining a fill status of a canister of fluid used with medical devices.

2. Description of Related Art

The treatment of open wounds and sores such as decubitis ulcers and those ulcers found on the feet of diabetics is problematic. Proper treatment of such wounds which are frequently infected with bacterial pathogens is multifactorial. Surgery is usually required to remove dead and necrotic tissue. Antibiotics are used to inhibit the growth or kill the pathogenic bacteria, if possible. At the same time, proper nutrition is necessary to maintain the health status of the patient and more importantly, proper wound care is essential to healing of the wound or sore.

Proper wound care requires keeping the wound clean and dry. When the wound is infected, the underlying tissue expresses serous fluids and possibly a purulent exudate, both of which have to be removed to promote wound healing. Traditional methods of removing the aforementioned fluids required a mechanical scrubbing of the wound and drying of the wound with sponges. This procedure is not only painful for the patient but also increases the possibility of superinfection of the wound by bacteria introduced into the wound during treatment.

An alternative to this mechanical scrubbing of the open wound is a negative pressure wound closure device. This negative pressure wound closure device consists of a foam pad which is placed over the wound to form a relatively air tight and leak proof seal around the wound. The negative pressure wound closure device also has a vacuum pump fluidly coupled to the pad which is seated over the patient's wound. When the vacuum pump is activated, a negative pressure is created inside the pad covering the wound. The fluids expressed by the wound are removed through the foam pad by the negative pressure and transported through a tube connecting the foam pad to a canister. The canister collects the fluids removed from the wound. When the canister is full of fluid removed from the wound, the canister is emptied and reengaged to the vacuum system. Attempts have been made to alert the user when the canister is full of wound fluid. These methods have been aimed at directly measuring the amount of wound fluid in the canister.

However, existing methods of directly measuring the amount of wound fluid in the canister have proved unreliable because, generally, the wound fluid is viscous. The fluid also frequently foams, bubbles, and traps air, which may result in the fluid not settling to the bottom of the canister. There remains a need in the art for a reliable system and method to alert the user when the canister for collection of wound fluid is full and in need of emptying.

SUMMARY OF THE INVENTION

The problems with existing canister detection systems are solved by the systems and method of the present invention. In accordance with one embodiment of the present invention, a method for detecting a fill status of a canister of fluid in a tissue treatment system is provided. The method includes creating a reduced pressure in a fluid communication path of the tissue treatment system and applying the reduced pressure to a tissue site. Fluid is collected from the tissue site in the canister. The reduced pressure is released, and a decay of the reduced pressure is measured. A fill status of the canister is determined from the measured decay.

In another embodiment of the present invention, a reduced pressure treatment system includes a canister fluidly connected to a tissue site and configured to receive fluid drawn from the tissue site under the influence of a reduced pressure. A reduced pressure source is configured to provide the reduced pressure and is fluidly connected to the tissue site by a fluid communication path. The fluid communication path includes a source conduit, the canister, and a target conduit. The canister is positioned between the reduced pressure source and the tissue site and is fluidly connected to the reduced pressure source by the source conduit. The canister is also fluidly connected to the tissue site by the target conduit. The reduced pressure treatment system further includes a sensing device in communication with the source conduit and configured to sense a pressure in the source conduit. A valve is provided in communication with the source conduit to selectively vent the reduced pressure. A processing unit is in communication with the sensing device and the valve. The processing unit is configured to open the valve for a selected amount of time, receive sensing data from the sensing device during the selected amount of time to determine a decay of reduced pressure, and determine a fill status of the canister based on the decay of reduced pressure.

In still another embodiment of the present invention, a reduced pressure treatment system includes a reduced pressure source to provide a reduced pressure. A porous pad is positioned at the tissue site and is fluidly connected to the reduced pressure source. A canister is fluidly connected between the porous pad and the reduced pressure source to collect fluid drawn from the tissue site. The system further includes a solenoid valve that is fluidly connected to a conduit between the canister and the reduced pressure source. Means is provided for determining a pressure decay in the conduit when the solenoid valve is opened.

Other objects, features, and advantages of the present invention will become apparent with reference to the drawings and detailed description that follow.

DETAILED DESCRIPTION OF THE PREFERRED EMBODIMENT

In the following detailed description of the illustrative embodiments, reference is made to the accompanying drawings that form a part hereof. The invention may be practiced using these illustrative embodiments. These embodiments are described in sufficient detail to enable those skilled in the art to practice the invention. Other embodiments may be utilized, and that logical, structural, mechanical, electrical, and chemical changes may be made without departing from the spirit or scope of the illustrative embodiments. To avoid detail not necessary to enable those skilled in the art to practice the invention, the description may omit certain information known to those skilled in the art. Therefore, the following detailed description should not be taken as limiting. The scope of the illustrative embodiments is defined by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Although the terms "vacuum" and "negative pressure" may be used to describe the pressure applied to the tissue site, the actual pressure applied to the tissue site may be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

The term "tissue site" as used herein refers to a wound or defect located on or within any tissue, including but not limited to, bone tissue, adipose tissue, muscle tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that ma be harvested and transplanted to another tissue location.

Figure 1:
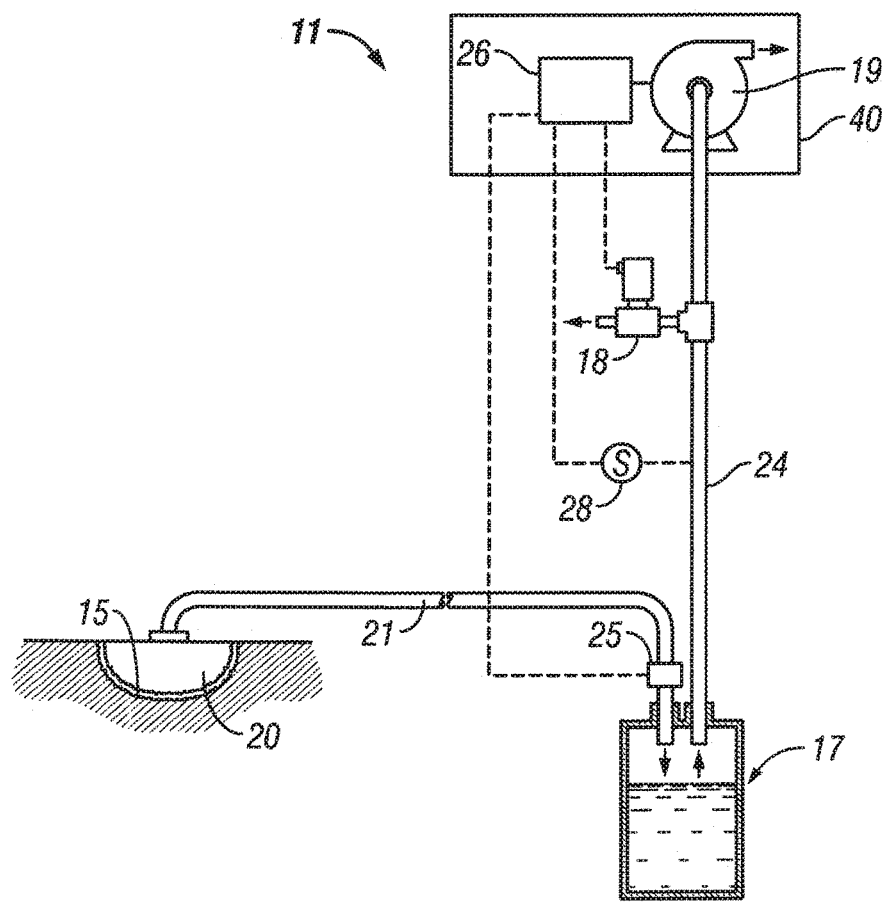
FIG. 1 depicts a reduced pressure treatment system having full canister detection capabilities according to an embodiment of the present invention.

Referring to FIG. 1, a reduced pressure treatment system 11 includes a porous pad 20, or other distribution manifold positioned at a tissue site 15. The porous pad 20 is fluidly connected to a canister 17 by a target conduit 21. A reduced pressure source 19 is fluidly connected to the canister 17 by a source conduit 24. In operation, the reduced pressure source 19 delivers a reduced pressure to the tissue site through a fluid communication path, which is collectively comprised of the source conduit 24, the canister 17, and the target conduit 21.

A solenoid or other suitable valve 18 is fitted to the source conduit 24 and serves to release the reduced pressure within the fluid communication path to the atmosphere when opened. The solenoid valve 10 may communicate with and be controlled by a processing unit 26, which is described in more detail below. The processing unit 26 may further communicate with a sensing device 28 that is used to determine a pressure in source conduit 24.

The reduced pressure treatment system 11 is capable of reliably determining the fill status of a canister (i.e. whether the canister is full or not full of fluid). The system 11 relies on the volume of the fluid communication path being fixed and thus, relief of the vacuum from this known volume should occur within a set time after the valve 18 is opened. When the processing unit 26 detects a blockage within the fluid communication path by any reliable blockage detection method, the processing unit 26 signals the valve 18 to open for a selected amount of time (e.g. 1 second) to vent the reduced pressure from the fluid communication path to atmosphere. The processing unit 26 receives sensing data from the sensing device 28 and monitors the pressure decay over this 1 second period. If the pressure decays quickly, then processing unit 26 determines that the canister 17 is full as the volume of the chamber being vented is small. Accordingly, the processing unit 26 will signal an alarm if a canister full status is determined.

If the decay is slow, which is to say that in the 1 second period that the solenoid valve 18 is opened, the vacuum does not decay to a pre-determined level, the processing unit 26 will conclude that the canister 17 is not full. The processing unit will then assume that the blockage condition originally detected is caused by an actual blockage in the target conduit 21 and not a canister full condition. The processing unit 26 in this particular instance may signal a separate alarm to indicate the presence of a blockage. Preferably, the alarms used to notify a user of a canister full of wound fluid and a blockage in the target conduit 21 through which the wound fluid flows are separate and distinct.

The decay of the reduced pressure may be determined in several ways. For example, the decay may be determined by measuring a reduction in the reduced pressure (i.e. increase in absolute pressure) over a selected amount of time after opening valve 18. As another example, the decay may be determined by measuring the amount of time that is required for the reduced pressure to drop to a threshold pressure. The decay in reduced pressure may also be determined by measuring the reduction in the flow rate in the source conduit 24 over the selected amount of time after opening valve 18. Other methods of measuring the decay of reduced pressure may also be used in a similar manner and are contemplated within the scope of the illustrative embodiments.

Additional components may be employed together with the illustrative embodiments to better determine the fill status of canister 17. For example, the target conduit 21 connecting canister 17 to the porous pad 20, through which wound fluids flow, may include optional valve 25. Closing valve 25 at the time of venting to atmosphere through valve 18 may indicate the volume within the canister that is empty. Deducing from this indication of empty volume and knowing the geometry of the canister, one may determine the level of fluid in the canister, and also may determine fluid flow rate from the tissue site 15 if periodically monitored.

Figure 2:
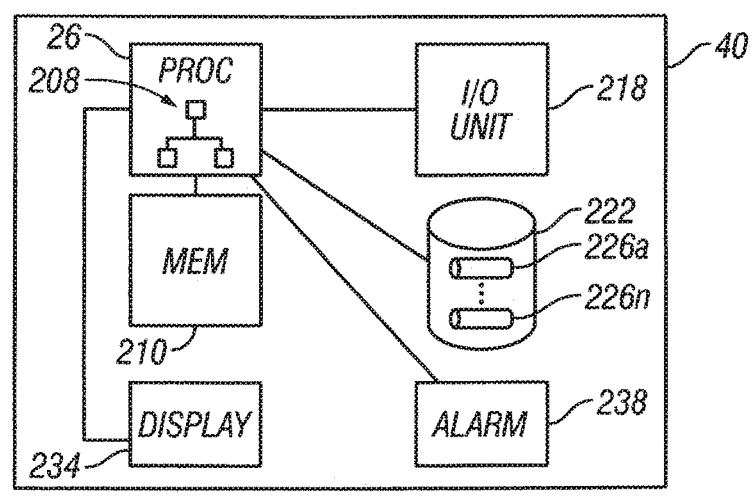
FIG. 2 depicts a block diagram of a processing unit of the reduced pressure treatment system of FIG. 1.

Referring still to FIG. 1, but also to FIG. 2, the processing unit 26 may be contained within a therapy unit housing 40 that may also house the reduced pressure source 19, the sensing device 28, and the valve 18. The processing unit 26 may be configured with one or more processors that are the same or different types. For example, the processing unit 26 may include one or more processors, logic, analog components, or any other electronics that enable signals including information, such as fluid pressure at various locations in the system to be received.

The processing unit 26 executes software 208 and may further be in communication with (i) a memory 210 for storing data and software code, (ii) an input/output (I/O) unit 218 for communicating with other devices and systems, such as a valves or sensing devices, wirelessly, via a wire, or via a memory input device, (iii) a storage unit 222 that may store one or more data repositories 226a-226n (collectively 226), such as a database having one or more files, (iv) an electronic display 234 that may or may not be touch-sensitive, and (v) one or more alarms 238 that are capable of signaling a user of the reduced pressure treatment system using audio, visual, or other signals. The software 208 may be configured to interface with each of the other devices (e.g., electronic display 234) to allow management and observation of the reduced pressure treatment.

Test Data

Figure 3:
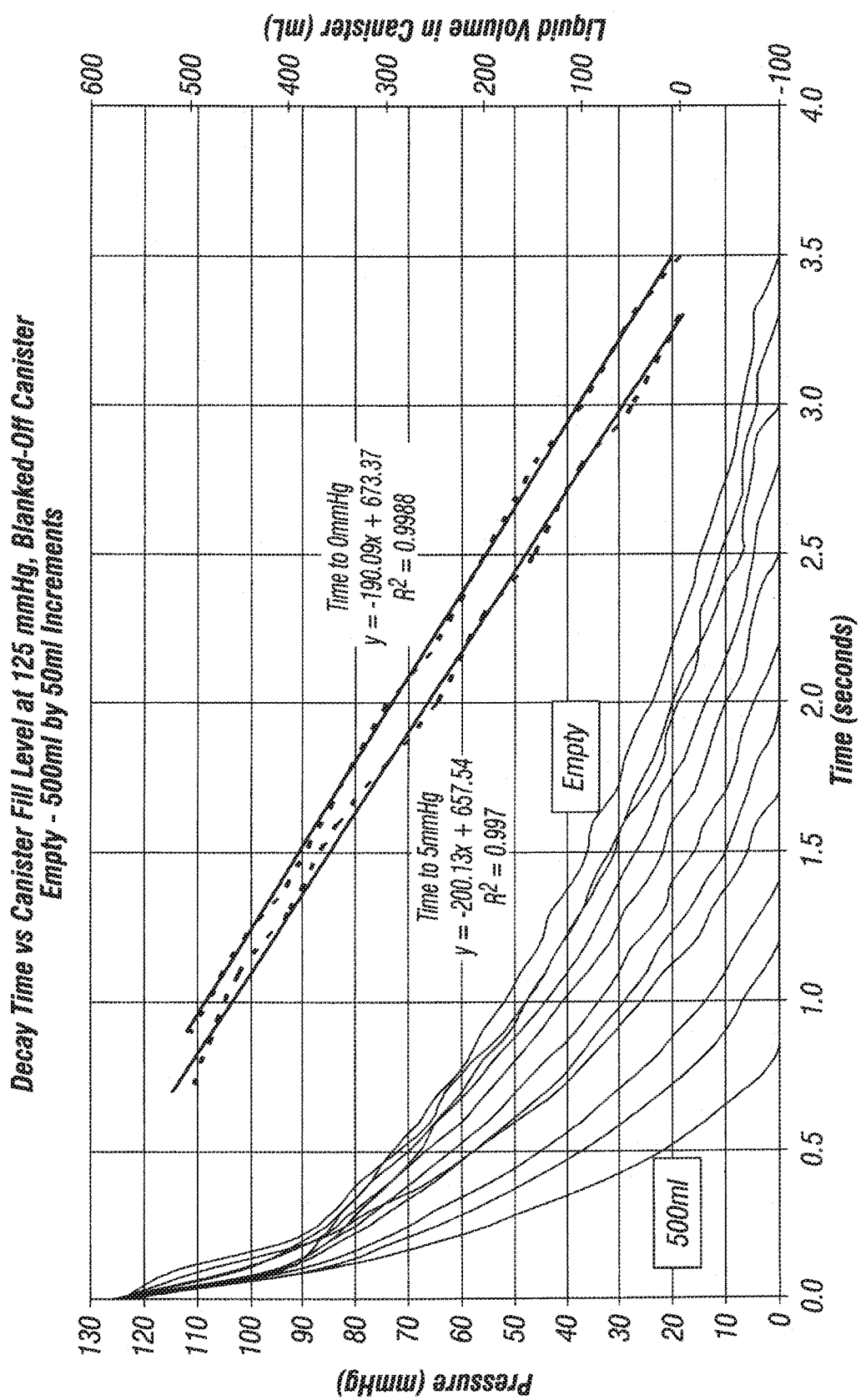
FIG. 3 depicts a graphical representation of the results of a test conducted with a system employing a full canister detection method according to an illustrative embodiment of the present invention.
Figure 6:
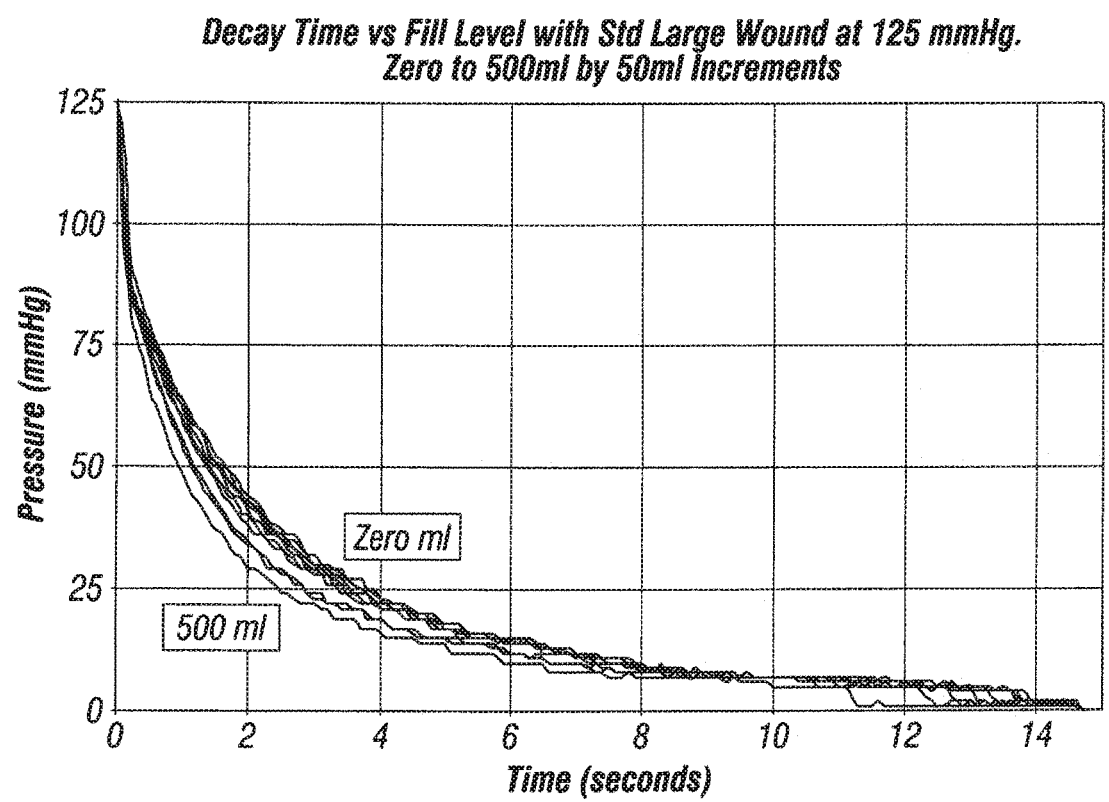
FIG. 6 depicts a graphical representation of the results of a test conducted with a system employing a full canister detection method according to an illustrative embodiment of the present invention.

With reference to FIG. 3, this figure depicts a graphical representation of the results of a test conducted with a system similar to reduced pressure treatment system 11. In this test, variation in decay time was noted against fill level at 125 mmHg for a closed canister. The canister was filled with various levels of water from empty to 500 ml in 50 ml increments. Negative pressure for the wound therapy was set to 125 mmHg and the system run until the pump stopped at slightly over the target pressure. Therapy was then turned off and natural leakage was applied to bring the pressure down to 125 mmHg. At this point, the valve was operated to vent the canister to atmosphere. The pressure profile was recorded at 10 samples per second. The same test was also conducted with a standard large wound attached to the system and resulted in the graphs of FIG. 6.

Figure 4:
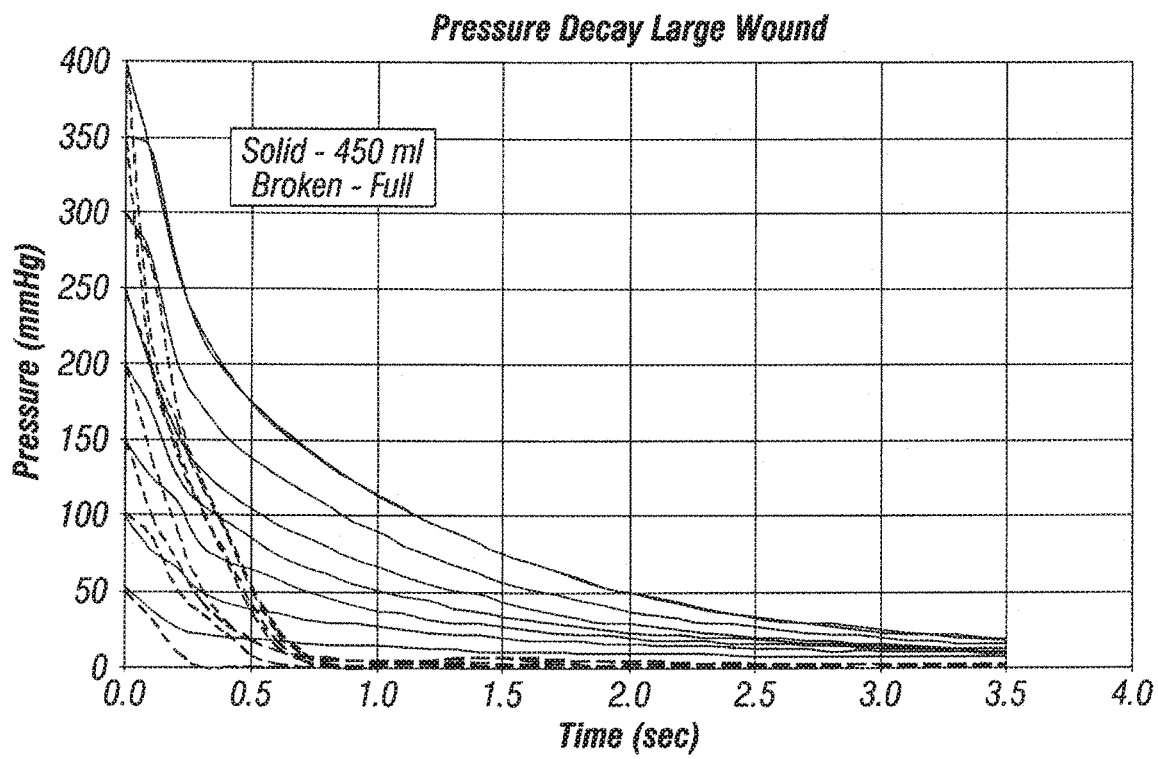
FIG. 4 depicts a graphical representation of the results of a test conducted with a system employing a full canister detection method according to an illustrative embodiment of the present invention.

Referring to FIG. 4, this figure depicts a graphical representation of the results of a test in which differences in decay times between full and nearly full canisters at various pressures with large wound were observed. A standard large wound foam and dressing was prepared on a plastic base and fitted with a reduced pressure delivery pad to allow a syringe to inject liquid so as to fill the canister and cause a blockage alarm. Two sets of curves were plotted at therapy pressures of 50 to 400 mmHg, one at 450 ml fluid level and one with a canister filled by wound drainage until a blockage alarm occurred. The 450 ml value was chosen because as high a fill level as possible was required for the specific canister used, consistent with no blockage alarm occurring. This situation was contemplated to be the worst case scenario with the understanding that if the system could differentiate between the two situations at a high level, it would only be easier as the level is reduced.

The canister was filled to 450 ml and a pressure slightly above the target pressure was acquired. The vacuum pump was turned off and as leakage brought the pressure down to the target level, the vent valve was opened as described above. For the blocked family of curves, the canister was filled by injecting water into the wound and running under normal therapy conditions. Results of this test are shown in FIG. 4.

Figure 5:
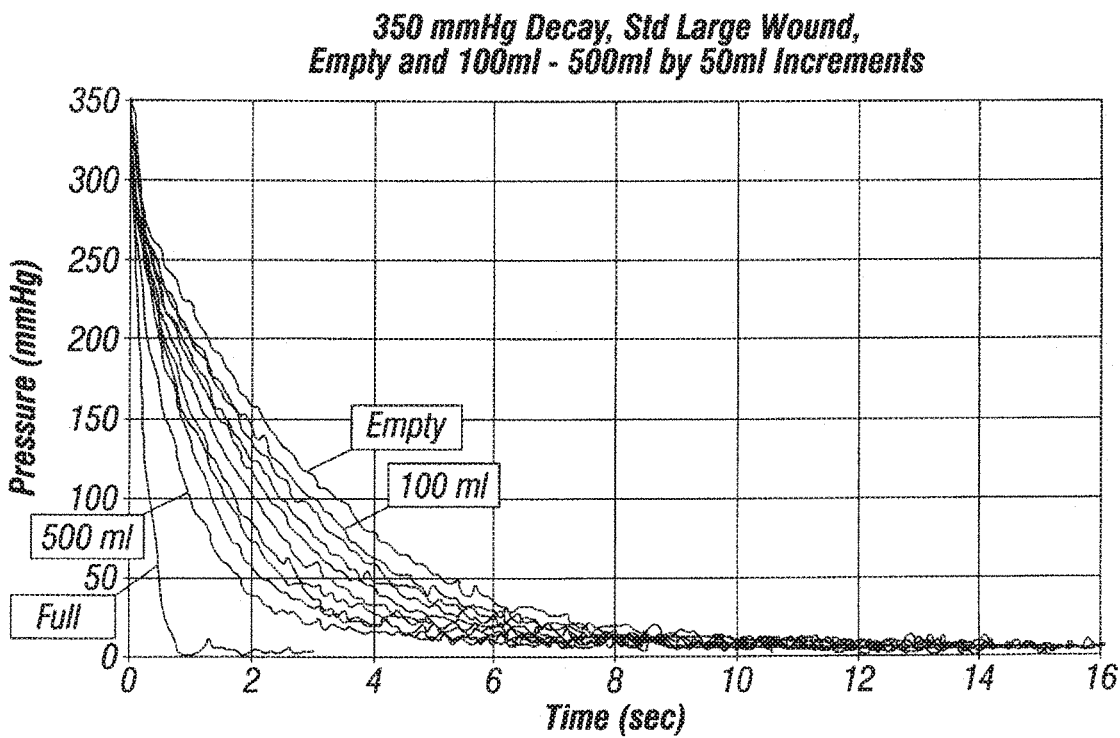
FIG. 5 depicts a graphical representation of the results of a test conducted with a system employing a full canister detection method according to an illustrative embodiment of the present invention.

With reference to FIG. 5, this figure depicts a graphical representation of the results of a test in which decay differences between full and other fluid levels at 350 mmHg with a large wound were observed. A standard large wound was prepared as in the test of FIGS. 3 and 4 and pressure curves plotted at 350 mmHg for fluid levels from empty to 500 ml, filling externally. This procedure was done under direct control as in the tests described above. The system was run under normal therapy at 200 mmHg and fluid injected into the wound until a blockage alarm occurred. Direct control was resumed at 350 mmHg and the last curve plotted.

Test Conclusions

The plots obtained with a closed canister in FIG. 3 show good linearity between the fill level and the time for the pressure to fall to both zero and 5 mmHg. There is some crossover in the early stages of the decay, but the trend of the plots appears to indicate that decay time is approximately proportional to fill level.

The results depicted in FIG. 3 were for a closed canister. Additional work as reflected in FIG. 6 revealed that when a wound is attached, the cross-over effect is considerably reduced.

The graph in FIG. 4 indicates that there is distinct grouping in the data. With a full canister when filter occlusion had occurred, the pressure fell to under 10 mmHg in less than 0.8 seconds, irrespective of the therapy pressure. When the canister is approximately full but occlusion had not occurred, the time to 10 mmHg was three seconds or more. The differential may have improved if the time to a percentage of initial rather than to an absolute pressure were measured.

FIG. 5 confirms that the decay times for all fill levels from empty to 500 ml take a substantial time to fall to near-zero levels from 350 mmHg. The fastest decay rate (500 ml) fell to about 20 mmHg after four seconds and was still around 10 mmHg after 10 seconds. By comparison, the blocked curve fell to virtually zero (under 3 mmHg) in less than a second.

The system and method disclosed in the instant application improves upon existing negative pressure treatment systems by reliably alerting the user of the system that the wound fluid canister is full and may have to be emptied. By releasing the pressure in the fluid communication path through a valve, the systems and methods disclosed herein are able to measure the decay of the negative pressure. If the negative pressure inside the fluid communication path decays rapidly, then the system determines that the canister is full and activates an alarm notifying the user that the canister is full of wound fluid. If the negative pressure inside the fluid communication path decays slowly, then the system determines that there is a blockage in the system that should be removed and notifies the user by activating an alarm.

Even though many of the examples discussed herein are applications of the present invention in the medical field of treatment of wounds, the present invention also can be applied to other types of negative pressure applications including but not limited to suction and fluid collection devices for other medical and non-medical uses.

One skilled in the art will see that the present invention can be applied in many areas where there is a need to provide an indication of a fill status of a container containing any substance. It should be apparent from the foregoing that an invention having significant advantages has been provided. While the invention is shown in only a few of its forms, it is not just limited but is susceptible to various changes and modifications without departing from the spirit thereof.

The invention claimed is:

1. An apparatus for determining a fill level of a container in a tissue treatment system, the apparatus comprising:
   a processing unit configured to:
   sense a reduced pressure in a source conduit;
   vent the reduced pressure in the source conduit for a select amount of time; and
   determine a fill level of the container based on a decay of reduced pressure in the source conduit over the selected amount of time.

2. The apparatus of claim 1, further comprising:
   a first valve in communication with the processing unit and fluidly connected to the source conduit.

3. The apparatus of claim 2, wherein the processing unit is configured to vent the reduced pressure in the source conduit for the selected amount of time by configuring the first valve to vent.

4. The apparatus of claim 3, further comprising:
   a second valve in communication with the processing unit and fluidly connected to a target conduit between the container and a tissue site.

5. The apparatus of claim 4, wherein the processing unit is configured to isolate the container when the first valve is venting by configuring the second valve to isolate.

6. The apparatus of claim 1, further comprising:
   a sensing device in communication with the processing unit and fluidly coupled to the source conduit.

7. The apparatus of claim 6, wherein the processing unit is configured to receive sensing data from the sensing device and based on the received sensing data calculate the decay over the selected amount of time.

8. The apparatus of claim 1, wherein the processing unit is configured to determine the decay based on the decay of reduced pressure over a fixed period of time.

9. The apparatus of claim 1, wherein the processing unit is configured to determine the decay based on measuring the amount of time it takes for the reduced pressure to reach a selected pressure threshold.

10. The apparatus of claim 1, wherein the processing unit is configured to determine the decay based on a reduction in a measured flow rate.

11. The apparatus of claim 1, wherein the processing unit is configured to receive geometry data for the container and based on the received geometry data determine the fill level of the container.

12. The apparatus of claim 1, wherein the processing unit is configured to receive geometry data for the container and based on the received geometry data determine a fluid flow rate for a tissue site.

13. An apparatus for determining a fill level of a container in a tissue treatment system, the apparatus comprising:
    a first valve configured to vent a reduced pressure in a source conduit; and
    a processing unit configured to:
    measure a decay of reduced pressure in the source conduit if the first valve is configured by the processing unit to vent the reduced pressure; and
    determine the fill level of the container from the decay of reduced pressure in the source conduit.

14. The apparatus of claim 13, further comprising:
    a sensing device in communication with the processing unit and fluidly connected to the source conduit, the processing unit configured to receive sensing data from the sensing device and based on the received sensing data calculate the decay over a selected amount of time.

15. The apparatus of claim 13, wherein the processing unit is configured to receive geometry data for the container and based on the received geometry data determine the fill level of the container.

16. The apparatus of claim 13, wherein the processing unit is configured to receive geometry data for the container and based on the received geometry data determine a fluid flow rate for a tissue site.

17. The apparatus of claim 13, further comprising:
    a second valve in communication with the processing unit and fluidly connected to a target conduit between the container and a tissue site.

18. The apparatus of claim 17, wherein the processing unit is configured to isolate the container when the first valve is venting by configuring the second valve to isolate.

* * * * *

UNITED STATES PATENT AND TRADEMARK OFFICE
CERTIFICATE OF CORRECTION

PATENT NO. : 10,765,592 B2
APPLICATION NO. : 15/812337
DATED : September 8, 2020
INVENTOR(S) : Christopher Brian Locke Page 1 of 1

It is certified that error appears in the above-identified patent and that said Letters Patent is hereby corrected as shown below:

On the Title Page

<u>On Page 4, Column 1, Under (Other Publications)</u>
Line 11, delete "Philidelphia," and insert -- Philadelphia, --, therefor.

<u>On Page 4, Column 2, Under (Other Publications)</u>
Line 36, delete "Björn" and insert -- Björn --, therefor.

<u>On Page 5, Column 1, Under (Other Publications)</u>
Line 1, delete "Hypermia" and insert -- Hyperemia --, therefor.

In the Specification

<u>Column 1</u>
Line 32, delete "decubitis" and insert -- decubitus --, therefor.

<u>Column 3</u>
Line 60, delete "ma" and insert -- may --, therefor.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*